United States Patent
Beese et al.

(10) Patent No.: US 9,347,912 B2
(45) Date of Patent: May 24, 2016

(54) SENSOR ADAPTER, METHOD FOR THE MANUFACTURE THEREOF, METHOD FOR THE USE OF A SENSOR IN THIS SENSOR ADAPTER AND BIOREACTOR WITH THIS SENSOR ADAPTER

(75) Inventors: Jochen Beese, Norderstedt (DE); Sven Eikelmann, Petershagen (DE); Jeff Watkins, Watchung, NJ (US); Rafael Kopla, Cranford, NJ (US)

(73) Assignee: Eppendorf AG (DE)

( * ) Notice: Subject to any disclaimer, the term of this patent is extended or adjusted under 35 U.S.C. 154(b) by 1374 days.

(21) Appl. No.: 12/840,844

(22) Filed: Jul. 21, 2010

(65) Prior Publication Data

US 2011/0111489 A1    May 12, 2011

(30) Foreign Application Priority Data

Nov. 6, 2009    (DE) .......................... 10 2009 052 266

(51) Int. Cl.

| C12M 1/00 | (2006.01) |
|---|---|
| C12M 3/00 | (2006.01) |
| G01N 27/404 | (2006.01) |
| C12M 1/34 | (2006.01) |

(52) U.S. Cl.
CPC ............ *G01N 27/404* (2013.01); *C12M 41/00* (2013.01); *Y10T 29/49002* (2015.01); *Y10T 29/49826* (2015.01)

(58) Field of Classification Search
CPC ... C12M 41/00; G01N 27/404; C12Q 1/6858; C12Q 2523/125; C12Q 2537/101; C12Q 2537/143; C12Q 1/6881; C12Q 1/6886; C12Q 2600/154; C12Q 2600/156; Y10T 29/49002; Y10T 29/49826

USPC ............ 435/29, 289.1, 286.1; 29/428, 592 A, 29/592.1

See application file for complete search history.

(56) References Cited

U.S. PATENT DOCUMENTS

| 3,659,586 A * | 5/1972 | Johns et al. ................... 600/354 |
|---|---|---|
| 3,702,806 A | 11/1972 | Olvia |
| 3,814,278 A | 6/1974 | Beierle |
| 3,870,602 A | 3/1975 | Froman et al. |
| 5,979,691 A | 11/1999 | Von Holdt |
| 2003/0168336 A1 * | 9/2003 | Downer et al. ................ 204/424 |
| 2005/0042133 A1 * | 2/2005 | Staphanos ........................ 422/50 |
| 2006/0205065 A1 | 9/2006 | Bossi et al. |
| 2008/0206847 A1 * | 8/2008 | Kunas et al. ................ 435/287.1 |

FOREIGN PATENT DOCUMENTS

| DE | 3404639 A1 | 8/1985 |
|---|---|---|
| EP | 09006409.8 | 5/2009 |

(Continued)

OTHER PUBLICATIONS

Dictionary.com—Definition of membrane (no date).*

*Primary Examiner* — Michael Marcheschi
*Assistant Examiner* — Shanta G Doe
(74) *Attorney, Agent, or Firm* — Barclay Damon, LLP

(57) ABSTRACT

A sensor adapter is described for the noninvasive positioning of a sensor, especially of an electrochemical sensor, in a medium. The sensor adapter comprises an accommodating channel, in which the sensor can be positioned and the one end region of which is closed off by a semipermeable membrane. Moreover, the sensor adapter comprises a hollow cylindrical sealing structure, which is disposed within the accommodating channel coaxially with the longitudinal axis of the latter and with which the sensor can be disposed gas tight adjacent to the semipermeable membrane.

16 Claims, 14 Drawing Sheets

(56) References Cited

FOREIGN PATENT DOCUMENTS

| | | |
|---|---|---|
| GB | 2114304 A | 8/1983 |
| WO | WO 94/19452 | 9/1994 |
| WO | WO 2007/134267 A2 | 11/2007 |
| WO | WO 2009/009771 A1 | 1/2009 |

* cited by examiner

SENSOR ADAPTER, METHOD FOR THE MANUFACTURE THEREOF, METHOD FOR THE USE OF A SENSOR IN THIS SENSOR ADAPTER AND BIOREACTOR WITH THIS SENSOR ADAPTER

CROSS REFERENCE TO RELATED APPLICATIONS

This application is based upon U.S. Ser. No. 61/258,863, filed Nov. 6, 2009 and German Patent Application No. DE102009052266.2, filed on Nov. 11, 2009, pursuant to relevant sections of 35 USC §119, the entire contents of each document herein being incorporated by reference.

TECHNICAL FIELD OF THE INVENTION

The present invention relates to a sensor adapter for the non-invasive positioning of a sensor in a liquid, to a method for manufacturing this sensor adapter, to a method for positioning a sensor in this sensor adapter and to a bioreactor in combination with this sensor adapter.

BACKGROUND OF THE INVENTION

Sensors are used to investigate liquids in different areas. These sensors comprise optical sensors or electrochemical sensors, in order to name only a few examples. The electrochemical sensors work according to an amperometric or potentiostatic measurement principle. Such a sensor is described, for instance, in GB 2 114 304.

Such sensors are placed in a liquid in order to determine certain properties. For example, they determine the cloudiness of the liquid, the oxygen content, the cell growth taking place or similar properties. A bioreactor, in which an above-mentioned sensor is disposed in the liquid used, is described in EP 09006409 and U.S. 61/177,389. In such bioreactors, the sensors are held with the help of pipe connections. These pipe connections are disposed, for example, at the cover of the bioreactor.

The sensors are attached over a press fit or a suitable adapter construction of the type described, for example, in DE 34 04 639. Depending on the fields of application of the liquid, the sensors are directly in contact with the liquid. In accordance with a different form of application, the contact between the sensor and the liquid is avoided, in order to exclude contamination of the liquid by the immersion of the sensor. For this purpose, the sensor is disposed in a tube, which is closed off; such a sensor is also described in EP 09006409 and U.S. 61/177,389. The tubes, used in this example of the application, are closed off by a stopper or a semi-permeable membrane. If the tube is closed off by a semi-permeable membrane, a dissolved oxygen (DO) sensor may be inserted therein for the purpose of determining the oxygen contents of the liquid in a noninvasive manner. For disposing the dissolved oxygen sensor suitably in the bioreactor, the corresponding connection cone is adapted to the cross-section of the dissolved oxygen sensor. Based on this construction, the dissolved oxygen sensor is held in the bioreactor by a frictional connection between the connecting cone and the dissolved oxygen sensor.

At the same time, with the help of the frictional connection, the dissolved oxygen sensor is to be sealed from the outside air. However, it has turned out that the frictional connection between the sensor and the connecting cone seals the interior of the tube only inadequately from the surroundings. An air slot between the sensor and the connecting cone, through which the outside air can penetrate into the tube of the sensor adapter, is already formed when the bioreactor is shaken or vibrated slightly. Additionally, air pressure variations in the environment generate fluctuations of the measured values. Thereby, the measurement of the oxygen concentration in the bioreactor is distorted and destabilized.

As a further disadvantage, it has turned out that, when the dissolved oxygen sensor is introduced into the connecting cone with tube, outside air is pushed in front of the dissolved oxygen sensor in the direction of the membrane.

It is therefore an object of the present invention to make available a sensor adapter, which, in addition to disposing the sensor in a noninvasive manner, also reduces the effects of the surroundings on the measured value determined by the sensor.

SUMMARY OF THE INVENTION

The above-named objective is accomplished by a sensor adapter for the noninvasive positioning of a sensor according to the claims. Moreover, the present invention discloses a bioreactor in combination with this sensor adapter. Moreover, a method is described for producing this sensor adapter. Furthermore, the present invention discloses a method for inserting or positioning a sensor in the above-named sensor adapter. Advantageous developments of the present invention and further developments and modifications are evident from the following description, the accompanying drawings and claims.

The sensor adapter for the noninvasive positioning of a sensor, especially an electrochemical sensor, in a medium has the following features: an accommodating channel, in which the sensor can be positioned and which is closed off in an end region by a semipermeable membrane, and a hollow, cylindrical sealing structure, which is disposed within the accommodating channel coaxially with the longitudinal axis thereof and with which the sensor can be disposed in a gas tight manner adjacent to the semipermeable membrane.

The sensor preferably is disposed in a plastic tube, preferably a silicone tube, which functions as an accommodating channel. Since the accommodating channel is closed off in an end region, which dips into the liquid that is to be investigated, the sensor can be positioned noninvasively in this way in the liquid. The hollow cylindrical sealing structure of the sensor adapter is disposed coaxially with the longitudinal axis of the accommodating channel in this accommodating channel. The geometry of the hollow cylindrical sealing structure is adapted to the dimensions of the sensor in such a manner that, when the sensor is inserted in the accommodating channel, a gas-tight connection is produced between the hollow cylindrical sealing structure and the sensor. This gas tight connection ensures that at least a partial volume of the accommodating channel is closed off in a gas-tight manner from the surroundings of the sensor adapter. Since the sensor is disposed within this gas-tight, closed off volume of the accommodating channel, any effect of the surroundings on the measurement of the sensor is prevented or at least reduced. Moreover, because of its construction, the hollow cylindrical sealing structure ensures a displacement of air or gas from the partial volume of the accommodating channel, which is to be closed off gas tight, while the sensor is being introduced into the accommodating channel. In this way, an optimum positioning of the sensor is ensured, since the effects of a medium, distorting the measurement, are minimized in the closed off partial volume of the accommodating channel.

In order to realize the above-described functions of the hollow cylindrical sealing structure, the latter preferably has a peripheral groove along at a radial inner wall and a sealing ring disposed in the groove. This sealing ring can be displaced in the axial direction within the peripheral groove. Furthermore, the cross-section of the peripheral groove is constructed in such a way, that the sealing ring can be disposed loosely in a first position in the groove and compressed between the sensor and an inner wall of the groove in a second position.

The peripheral groove of the sealing structure is open in the direction of the interior of the accommodating channel. Its function is to accommodate said sealing ring, so that the latter protrudes at least partly into the interior of the accommodating channel. As soon as the sensor is inserted in the accommodating channel, a press fit of the sealing ring on the sensor develops. Because of this press fit, the sealing ring is shifted within the groove between the first position and the second position as a function of the direction of movement of the sensor within the accommodating channel. The different geometries of the groove in the first and second positions, in combination with the geometric expansion of the sealing ring, ensure that the hollow cylindrical sealing structure forms a one-way valve. If the sealing ring namely is in its first position, air can be displaced by the sensor from the accommodating channel. This air escapes through a space between the inner wall of the groove and the sealing ring, since the sealing ring, when in the first position, does not fill up the groove completely. If the sealing ring is shifted into the second position by the movement of the sensor, a partial region of the accommodating channel is closed off gas tight. In the second position moreover, the sealing ring is compressed between the inner wall of the groove and the sensor in such a manner, that the escape of the medium, enclosed in the accommodating channel, is not possible.

For the purpose of supporting the displacement of the medium from the accommodating channel further, preferably at least one connecting channel, which is connected with the groove, is provided at the front side of the sealing structure facing the membrane. This connecting channel represents a flow connection with the groove. Air, for example, can escape through this connecting channel when the sealing ring is in its first position.

Depending on the length of the sealing structure parallel to the longitudinal axis of the accommodating channel, the sealing structure also forms a supporting sleeve. The sealing structure or supporting sleeve preferably is disposed in the end region of the accommodating channel, so that the latter can be supported laterally. This supporting function ensures that the accommodating channel is held dimensionally stably, for example, in the interior of the bioreactor. On this basis, a change in shape of the accommodating channel, for example, because of surrounding pressures, is avoided.

Furthermore, the present invention discloses a method for inserting the sensor in the sensor adapter, which has been described above. This method has the following steps: inserting the sensor in the accommodating channel, shifting the sealing ring into the first position by pushing the sensor into the accommodating channel, displacing a medium from the accommodating channel in that the sensor is moved in the direction of the membrane, and moving the sensor in the direction away from the membrane, so that the sealing ring is shifted into the second position and seals the sensor in the accommodating channel. With the help of this insertion method, it is ensured that an interfering volume of gas, for example in the end region of the accommodating channel, is displaced from the accommodating channel. The purposeful movement of the sensor in the accommodating channel displaces the sealing ring initially into its first position and then into its second position. By these means, a distorting gas volume is displaced to begin with and, after that, the partial volume of the accommodating channel is closed off gas tight. Without this gas tight closure, an interfering medium could flow into the end region of the accommodating channel, for example, in the event of vibrations.

It is furthermore preferred to move the sensor at least so far, that it contacts the membrane of the accommodation channel, preferably deforming it elastically, in order to displace the medium between the sensor and the membrane from the accommodation channel.

Moreover, the present invention discloses a method for producing the sensor adapter described above. This production method has the following steps: providing a plastic tube, shaping a hollow cylindrical sealing structure, inserting the sealing structure in the plastic tube coaxially with the longitudinal axis of the latter and closing off an end region of the plastic tube with a semipermeable membrane. In a special embodiment of this production method, the hollow cylindrical sealing structure with a peripheral groove at a radial inner wall is injection molded and a sealing ring is disposed in this groove. Alternatively, the hollow cylindrical sealing structure is produced by a cutting method as for example by milling. Further, all methods are applicable by means of which the described shape of the hollow cylindrical sealing structure can be produced. Furthermore, preferably a hollow cylindrical end sleeve is shaped and closed off at a face side by a semipermeable membrane. This hollow cylindrical end sleeve is slipped on to an end region of the accommodating channel in order to close of the latter. By these means, the accommodating channel is closed off by a semipermeable membrane. Moreover, for this closing off, the hollow cylindrical end sleeve preferably is disposed adjacent to the hollow cylindrical sealing structure, so that the two are separated from one another only by the plastic tube lying in between. Based on this construction, the sealing structure and the end sleeve support one another laterally over the plastic tube. This stabilizes the sensor adapter and, in particular, the plastic tube, so that the latter is better able to withstand any deformation by external influences.

It is also preferred if the sealing structure is closed off at the front side by the membrane. In this case, the production and installation of the end sleeve can be omitted because the sealing structure with membrane closes off the accommodating channel.

A further alternative of the inventive sensor adapter comprises an accommodating channel in which the sensor can be positioned and the end region of which is closed off by a semipermeable membrane wherein the semipermeable membrane has an elastically expandable cavity in which the sensor can be disposed in such a way that the semipermeable membrane tightly encloses the received part of the sensor.

According to this alternative, the semipermeable membrane realizes a tight enclosure of at least a part of the sensor in said sensor adapter. To this end, the semipermeable membrane forms a type of bag or pocket to receive the sensor. Since this pocket or cavity of said membrane is elastically deformable, the membrane sits closely onto the outside of the sensor. Thereby, the membrane forms a type of coating of the sensor which seals said sensor with respect to the environment. In order to guarantee the sealing or close fit of the membrane onto the sensor, the expandable cavity of the membrane has a diameter perpendicular to the longitudinal axis of the accommodating channel being smaller than the inner diameter of the accommodating channel, preferably than the outer diameter of the sensor to be positioned. It is further preferred that the diameter of the cavity perpendicular to the longitudinal axis of the accommodating channel is within a range of 90 to 30% of the inner diameter of the accommodating channel, preferably 80 to 30% or 70 to 30% or 60 to 40% of the inner diameter of the accommodating channel.

According to further embodiments of the above described sensor adapter, the membrane is integrally connected to the accommodating channel or the membrane is attached to a hollow cylindrical cap by means of which the accommodating channel can be closed off at one side.

Further, the present invention comprises a method for inserting a sensor in the above described sensor adapter having the following steps: pushing the sensor into the accommodating channel, pushing the sensor in the elastically expandable cavity of the membrane so that the sensor is at least partially and tightly enclosed by said membrane. In this context, it is preferred to move the sensor in said elastically deformable cavity of the membrane until the membrane abuts an end face of the sensor which is directed to the membrane.

Furthermore, a method for producing the above described sensor adapter is disclosed. It comprises the following steps: providing a plastic tube, closing off an end region of the plastic tube by means of a semipermeable membrane comprising an expandable cavity which extends in an axial direction of the plastic tube. Preferably, a hollow cylindrical cap is made which is closed off at one end face of said cap by means of the semipermeable membrane having the elastically expandable cavity. Said end cap is then attached to the end region of the plastic tube. According to a further preferred production alternative, the semipermeable membrane with an expandable cavity is made and then attached to the end region of the plastic tube directly.

BRIEF DESCRIPTION OF THE DRAWINGS

The preferred embodiments of the present invention are explained in greater detail with reference to the accompanying drawing in which.

DETAILED DESCRIPTION OF THE INVENTION

The present invention comprises a sensor adapter 10, which is used for positioning a sensor 5 in a medium 9 that is to be investigated. The sensor adapter 10 accommodates the sensor 5, so that the medium, which is to be investigated, does not come into contact with the sensor 5. On this basis, the sensor 5 can be inserted, positioned, removed and exchanged noninvasively with respect to the medium that is to be investigated.

Figure 1:
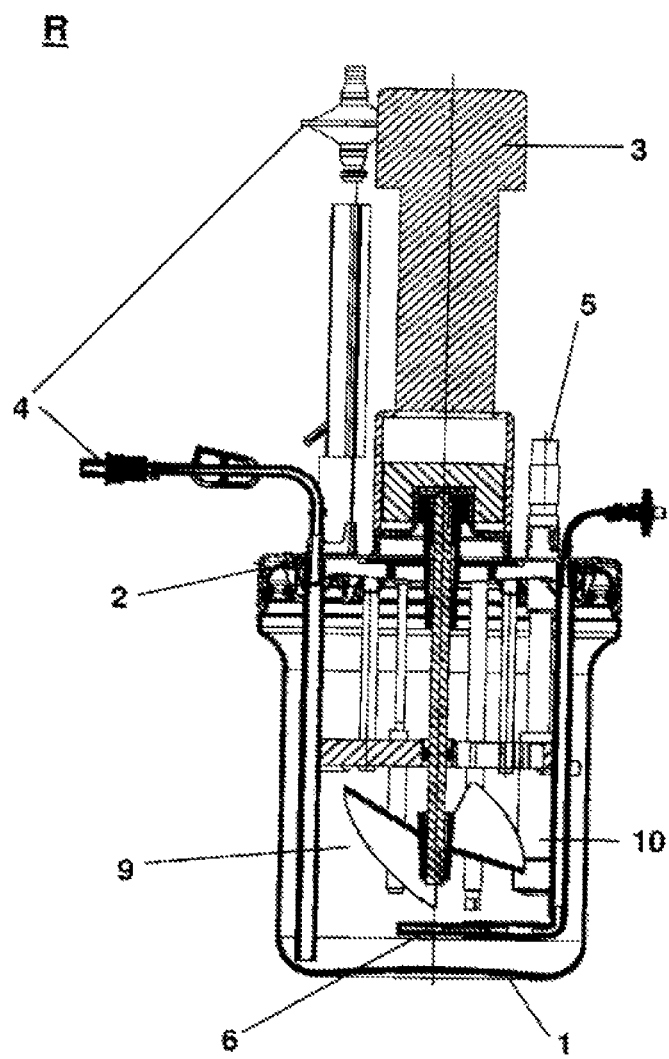
FIG. 1 shows a preferred embodiment of a bioreactor in a sectional representation.

The inventive sensor adapter 10 preferably is used in combination with a bioreactor R, similar to that shown in FIG. 1. The bioreactor R is known as a one-way system and as a multiway system. It consists of a container 1 with a cover 2. Such bioreactors R are described, for example, in EP 09006409 and U.S. 61/177,389 which are incorporated in their entirety herewith by reference.

The bioreactor R comprises different components, which are attached to the cover 2. These components include, for instance, a stirrer 3, pipelines 4 for liquids and/or gases, a dissolved oxygen sensor 5 as well as a sensor adapter 10.

In a preferred embodiment of the present invention, the function of the sensor adapter 10 is to accommodate the dissolved oxygen sensor 5 optimally in the bioreactor R. Preferably, with the help of the sensor adapter 10, other sensors are also disposed in the bioreactor R or generally in any medium, which is to be investigated.

Figure 2:
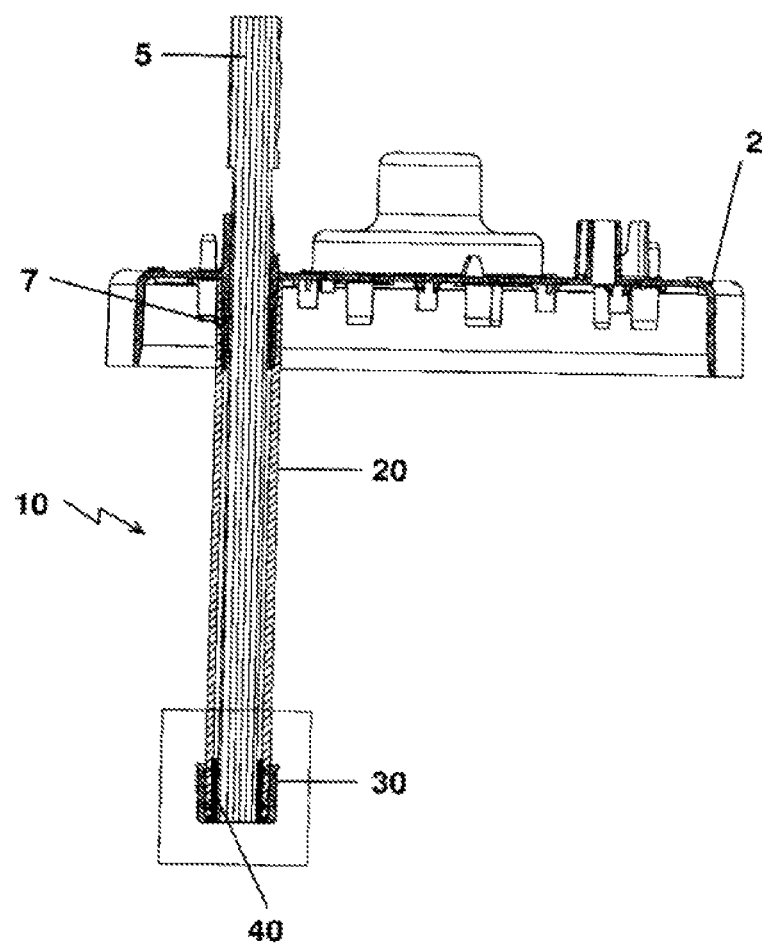
FIG. 2 shows a sectional representation of a cover of a bioreactor with sensor adapter.

The construction and function of the sensor adapter 10 is explained in the following by means of an example of a dissolved oxygen sensor 5, which is disposed in the bioreactor R. For this purpose, FIG. 2 shows an enlarged representation of the cover 2 of the bioreactor R of FIG. 1.

The sensor adapter 10 is attached to the connecting cone 7 of the cover 2, for example, by means of a press fit, in that an accommodating channel 20 is pushed onto the connecting cone 7. The sensor 5 is disposed within the accommodating channel 20. The accommodating channel 20 of the sensor adapter 10 preferably is formed by a plastic tube. In accordance with one embodiment, the accommodating channel 20 is a silicone tube. Moreover, in the end region facing away from the cover 2, the accommodating channel 20 is closed off by means of a membrane 32, preferably a semipermeable membrane. The membrane 32 may consist of different known materials. In conjunction with the dissolved oxygen sensor 5, silicone was used as semipermeable membrane 32 because it is permeable to oxygen.

Figure 3:
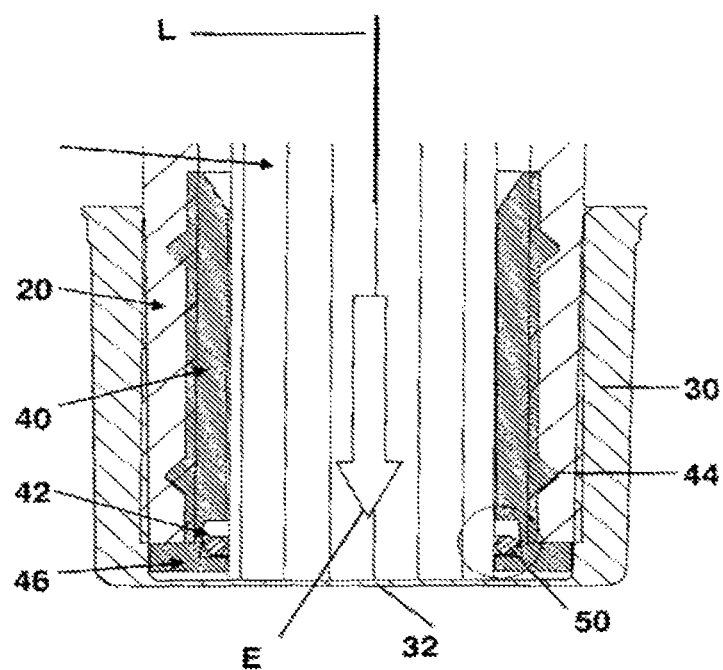
FIG. 3 shows an enlarged sectional representation of a preferred end region of the sensor adapter of FIG. 2.
Figure 5:
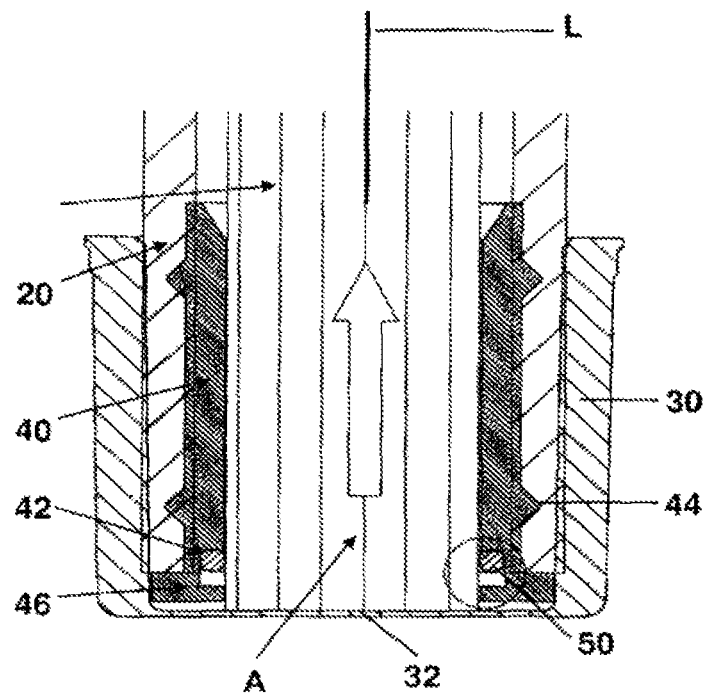
FIG. 5 shows an enlarged representation of an end region of a preferred sensor adapter.

In order to close off the accommodating channel 20 in accordance with different preferred embodiments, the membrane 32 is fastened directly at the accommodating channel 20, at a hollow cylindrical cap 30 or at a hollow cylindrical sealing structure 40 (compare FIGS. 3 and 5).

The hollow cylindrical sealing structure 40 is disposed within the accommodating channel 20 coaxially with the longitudinal axis of the latter. The hollow cylindrical sealing structure 40 is positioned at a convenient position along the length of the accommodating channel 20. For example, such a position is half way between the cover 2 and the end region of the accommodating channel 20, which is facing away from the cover 2. Likewise preferably, the hollow cylindrical sealing structure 40 may be disposed in the end region of the accommodating channel 20, as shown, for example, in FIG. 2.

Independently of its position, the sealing structure 40, aside from a sealing function (see below), also fulfills a supporting function. Because of its hollow cylindrical shape, the sealing structure 40 supports the accommodating channel 20 laterally and/or radially to the outside. For example, if a medium under pressure acts on the accommodating channel 20, deformation of the accommodating channel 20 is prevented or reduced by the supporting effect of the hollow cylindrical sealing structure 40. If the sealing structure 40 is remotely disposed from the end region of the accommodating channel 20, it fulfills the sealing structure in the same way described below for an arrangement in the end region of the accommodating channel 20.

In accordance with the representation in FIG. 2, the hollow cylindrical sealing structure 40 is positioned in the end region of the accommodating channel 20. So that it can maintain its position in the accommodating channel 20, the sealing structure 40 comprises fastening projections 44, which are directed radially to the outside. These fastening projections 44 are anchored in the accommodating channel 20 and in this way ensure that the sealing structure 40 is seated firmly. For example, these fastening projections 44 are constructed as pointed projections or barbs.

According to the preferred embodiment shown in FIGS. 2 and 3, the cap 30 closes off the accommodating channel 20. For this purpose, a semipermeable or other membrane 32 is fastened to the cap 30. Moreover, the cap 30 also has a hollow cylindrical shape, which makes possible the press fit of the cap 30 on the accommodating channel 20. Moreover, the cap 30 is supported radially at the sealing structure 40, preferably, over the accommodating channel 20 and/or directly over a front side flange 46 of the sealing structure 40 (compare FIGS. 3 and 5).

In accordance with an embodiment, which is not shown, the membrane 32 is fastened to the sealing structure 40. Accordingly, for this construction the cap 30 can be omitted for closing off the sensor adapter 10.

With reference to FIGS. 3 to 6, a peripheral groove 42 is disposed at the radial, inner wall of the sealing structure 40. Within the peripheral groove 42, there is a sealing ring 50. The sealing ring 50 preferably is formed by an O-ring of rubber or of different elastically deformable materials. Moreover, the internal diameter of the sealing ring 50 is sufficiently large so that the sealing ring 50 makes tight contact peripherally with the sensor 5 inserted in the accommodating channel 20.

Figure 4:
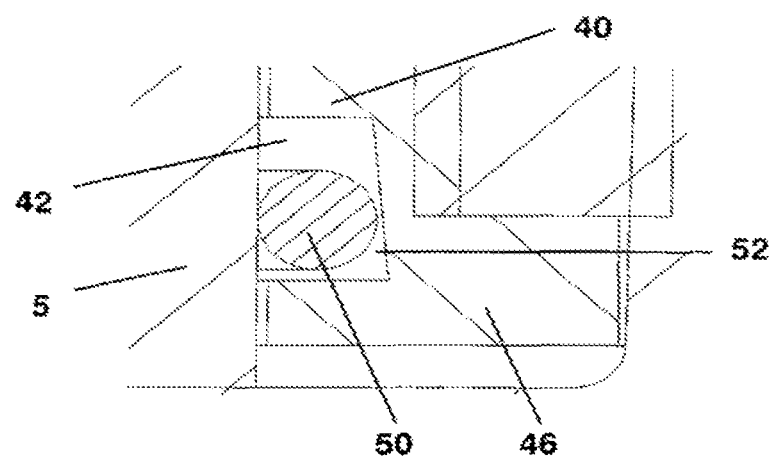
FIG. 4 shows an enlargement of a section from FIG. 3.
Figure 6:
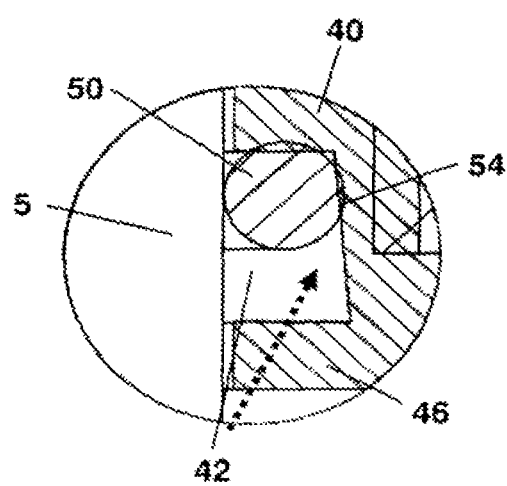
FIG. 6 shows an enlargement of a section of FIG. 5.
Figure 7:
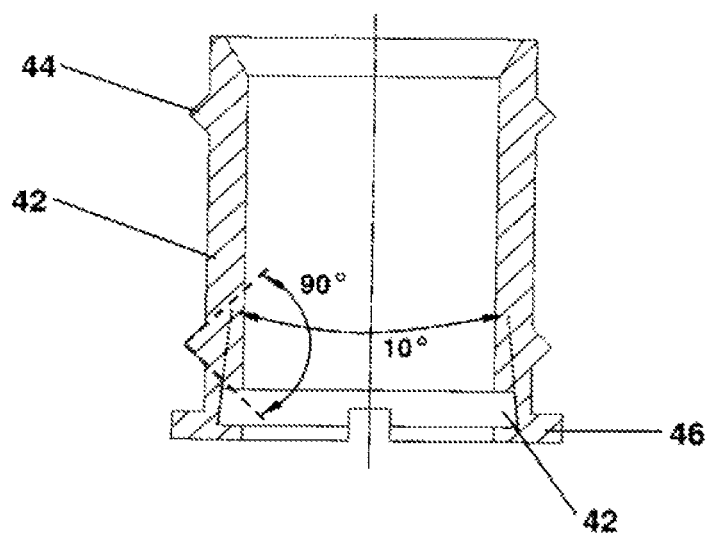
FIG. 7 shows a preferred embodiment of the hollow cylindrical sealing structure in a sectional representation.

In its extent parallel to the longitudinal axis of the sealing structure 40, the groove 42 is larger than the cross-section of the sealing ring 50, as illustrated in FIGS. 4 and 6. This axial extent of the groove 42 ensures that the sealing ring 50 can be shifted in the axial direction of the sealing structure 40 between a first 52 and a second position 54. In the axial direction of the sealing structure 40, the first position 52 and the second position 54 are disposed adjacent to one another, the first position 52 being closer than the second position 54 to the membrane 32.

The depth of the groove 42 in the radial direction of the sealing structure 40 is different in the two positions 52 and 54. In the first position 52, the groove 42 is deeper than the cross-section of the sealing ring 50. Because of this dimension, there is a gap between the sealing ring 50 and the radially adjacent inner wall of the groove 42, through which air, for example, can escape (compare FIG. 4).

In the second position 54, the groove 42 is not as deep as the cross-section of the sealing ring 50. For this reason, the sealing ring 50 is compressed in the second position 54 between the sensor 5 and the radial inner wall of the groove 42. The volume of the accommodating channel 20 between the sealing ring 50 and the membrane 32 is closed off gas tight in this way.

The radial inner wall of the groove 42 extends preferably in comparison to the longitudinal axis of the sealing structure 40. It is also conceivable that the radial, inner wall has a wavy construction, so that depressions are present in positions 52, 54. The function of this depression in the second position 54 is to accommodate the sealing ring 50.

Figure 8:
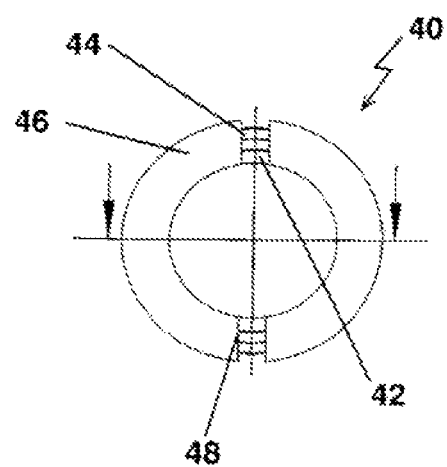
FIG. 8 shows a view of a face side of the sealing structure of FIG. 7.

According to a further, preferred embodiment, the sealing structure 40 includes a front side flange 46. The front side flange 46 comprises at least one and preferably a plurality of connecting channels 48 to the groove 42. This connecting channel 48 establishes a connection between the groove 42 and the volume of the accommodating channel 20 between the sealing ring 50 and the membrane 32. When the sensor 5 is inserted in the sealing structure 40, air from the volume between the sensor 5 and the membrane 32 is displaced. This air leaks away through the groove 42 directly and/or over the connecting channel 48 and the groove 42 into the region of the accommodating channel 20 above the sealing ring 50. According to the preferred embodiment of the connecting channel 48, shown in FIG. 8, said connecting channel 48 is constructed in the form of a slot. The slot 48 breaks through the flange 46 in the radial direction. Preferably, the connecting channel 48 likewise passes through the flange 46 in the axial direction of the sealing structure 40 (not shown). Moreover, several connecting channels 48 are distributed along the periphery of the flange 46.

Figure 10:
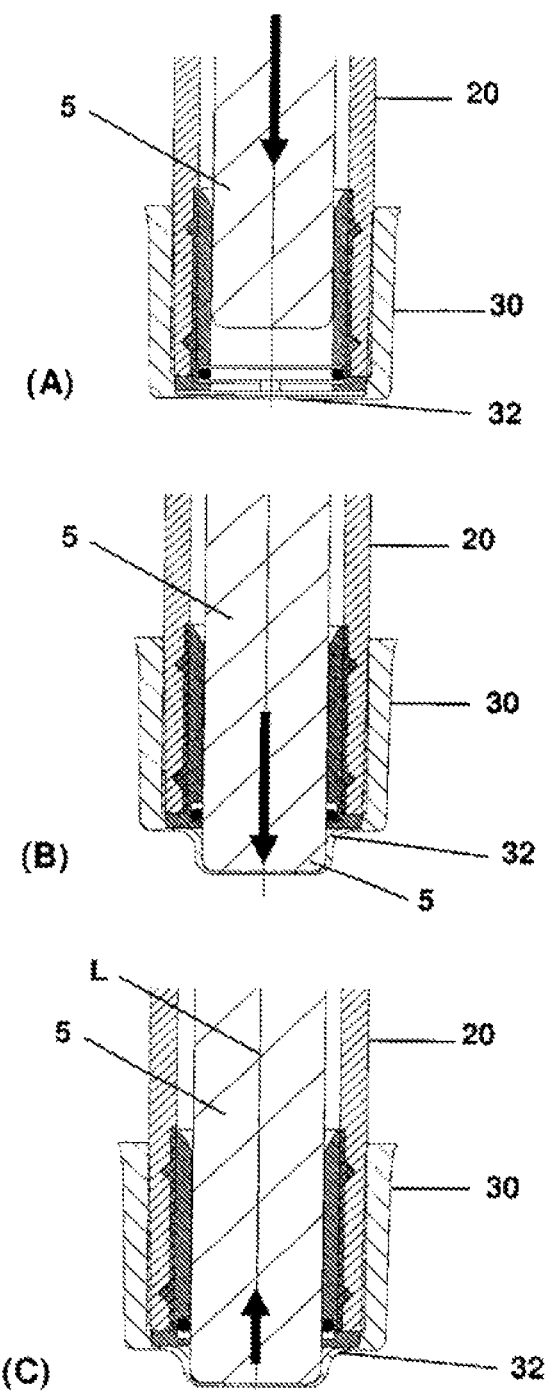
FIG. 10 shows a preferred representation of sequences of the process of inserting the sensor in the sensor adapter.
Figure 11:
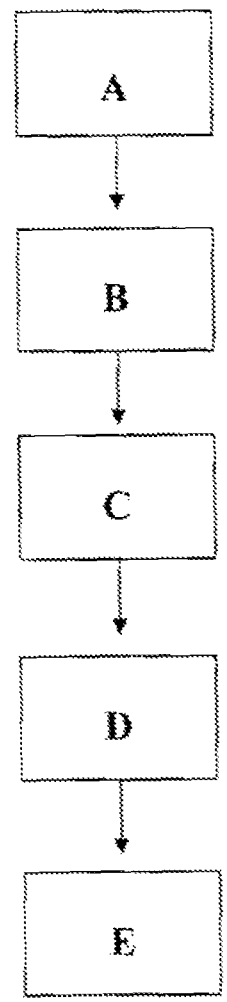
FIG. 11 shows a flow diagram of a preferred method of installing the sensor in the sensor adapter.

The insertion of the sensor 5 in the sensor adapter 10 is described with reference to FIGS. 10 and 11. To begin with, in step A, the sensor 5 is pushed into the accommodating channel 20 in the direction of the arrow of FIG. 3. As soon as the sensor 5 has reached the groove 42 with the sealing ring 50, the latter is moved by the sensor 5 within the groove 42 into the first position 52 (step B). While the sensor 5 is being moved further in the direction of the membrane 32, air is displaced from the volume of the accommodating channel 20 between the sealing ring 50 and the membrane 32. This air escapes through the gap between the sealing ring 50 and the radial inner wall of the groove 42 in the first position 52 (compare FIG. 4). Preferably, the escape of the air is also supported by the connecting channel 48 in the flange 46 (step C) (compare FIG. 10A).

According to a preferred embodiment, which is illustrated in FIG. 10B, the sensor 5 is moved at least until it touches the membrane 32. Preferably, the sensor 5 is moved even further in the axial direction of the accommodating channel 30 towards the membrane 32, so that the latter is deformed elastically. Based on this further movement and the elastic deformation of the membrane, it is achieved that much of the air from the volume between the sealing ring 50 and the membrane 32 is displaced (step D).

Subsequently, the sensor 5 is moved in the direction away from the membrane 32 (step E), as indicated by the arrow in FIG. 5. The sealing ring 50 is shifted into the second position 54 by this movement of the sensor 5. Preferably, this movement of the sensor in the direction of the arrow of FIG. 5 is supported by the elastic recovery of the previously deformed membrane 32. In this way, the membrane 32 returns to a state, in which it is stressed less and which is illustrated in FIG. 10C. Since the sealing ring 50 is now in its second position 54, the sensor 5 is sealed in the accommodating channel 20. The sealing to prevent penetration of gases from the surroundings into the region between the sealing ring 50 and the membrane 32 ensures that the determination of measured values by the sensor 5 is not distorted by surrounding factors.

From the movement of the sealing ring 50 within the groove 42 of the sealing structure 40, it can be seen that the sealing structure 40 makes a check valve available. Air can escape when the sealing ring 50 is in its first position 52. The volume between the sealing ring 50 and the membrane 32 is not closed off tightly. Air cannot escape when the sealing ring 50 is in its second position 44. Especially the tip of the sensor is then enclosed gas tight in the volume of the accommodating channel 20 between the sealing ring 50 on the membrane 32.

Figure 9:
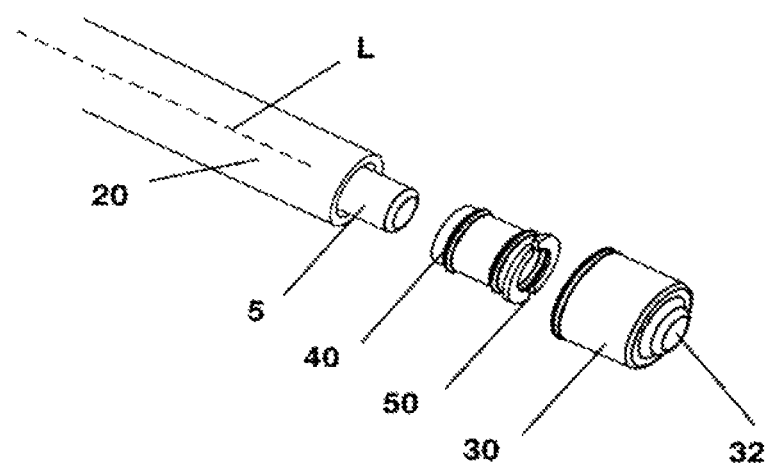
FIG. 9 shows an exploded view of the preferred sensor adapter with sensor.
Figure 12:
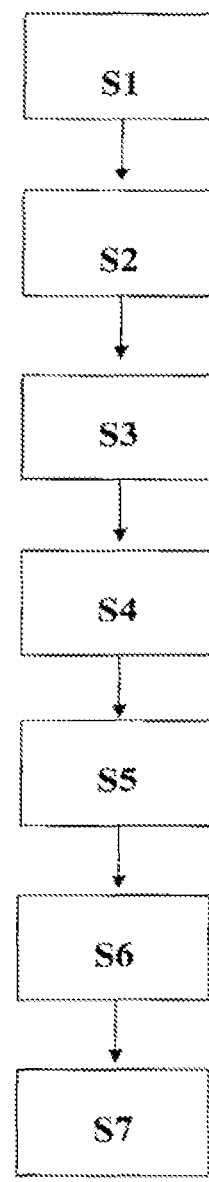
FIG. 12 shows a flow diagram of a preferred method of producing the sensor adapter.

FIG. 9 shows the sensor adapter 10 of a preferred embodiment in an exploded view. This comprises the accommodating channel 20, the sensor 5, the sealing structure 40, the sealing ring 50 and the cap 30 with the membrane 32. For producing the sensor adapter 10 of FIG. 12, initially, in step S1, the plastic tube 20 is prepared. Moreover, the hollow cylindrical sealing structure 40 is formed. According to one embodiment, the hollow cylindrical sealing structure 40 with the peripheral groove 42 in the radial inner wall is injection molded (S2). Alternatively, the hollow cylindrical sealing structure is produced by means of a cutting method, as for example milling. Further, all production methods can be used by means of which the described shape of the hollow cylindrical sealing structure can be produced. Moreover, in step S3, the sealing ring 50 is disposed in this groove 42.

After it is prepared, the sealing structure 40 is inserted in step S4 into the plastic tube 20 coaxially with the longitudinal axis of the latter. After that, the end region of the plastic tube 20 is closed off in step S7 with the help of a semipermeable membrane 32.

Preferably, a hollow cylindrical end sleeve 30 is shaped in step S5, in order to close off the plastic tube 20. This hollow cylindrical end sleeve 30 is then closed off at a face side by a semipermeable membrane 32 (step S6). Furthermore, in step S4, the hollow cylindrical sealing structure 40 preferably is disposed or inserted in the end region of the plastic tube 20. After that, in step S7, the hollow cylindrical end sleeve 30 is fastened in the end region of the plastic tube 20, so that the sealing structure 40 and the end sleeve 30 support one another radially over the plastic tube 20.

Figure 13:
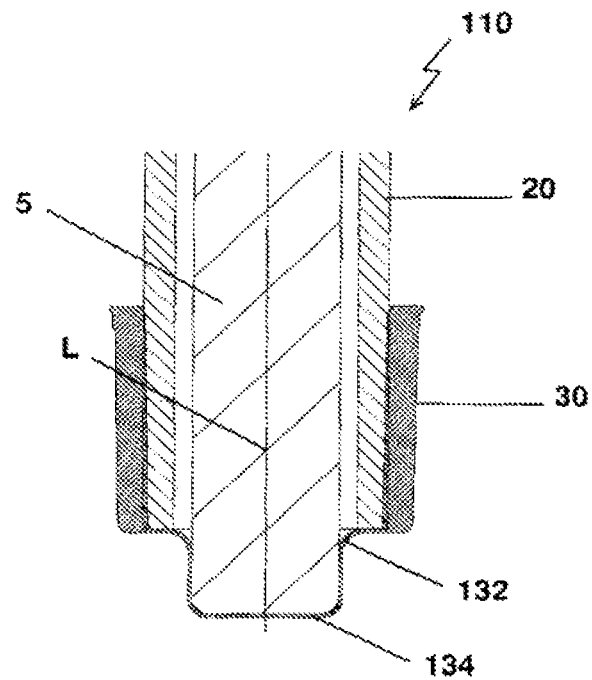
FIG. 13 shows an enlarged sectional representation of an end region of a further preferred sensor adapter.
Figure 14:
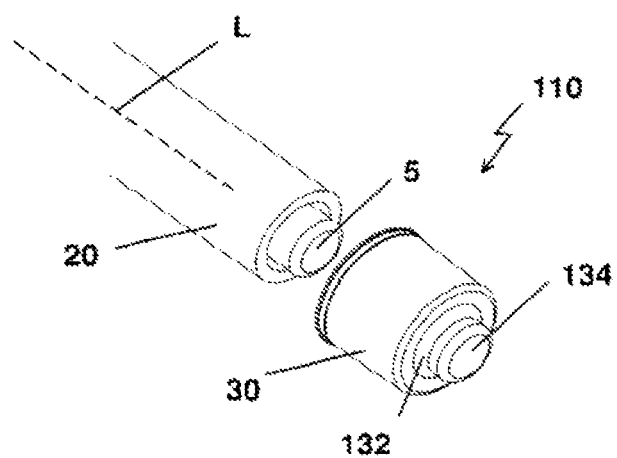
FIG. 14 shows an exploded view of the preferred sensor adapter with sensor according to FIG. 13.
Figure 15:
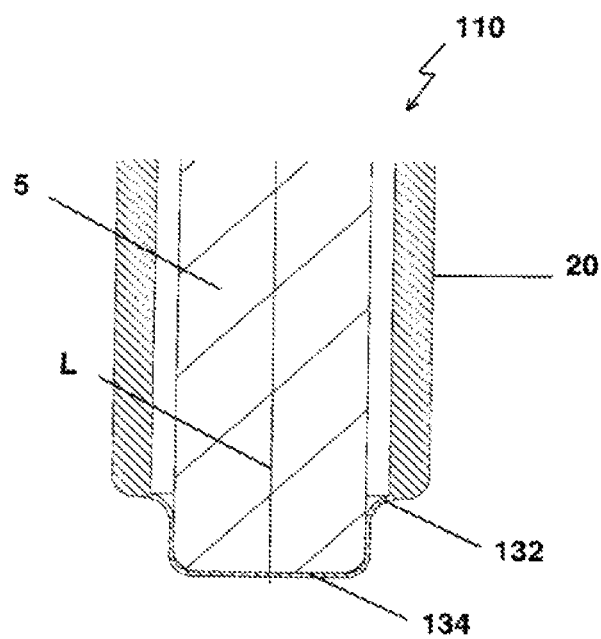
FIG. 15 shows an enlarged sectional view of an end region of the further preferred sensor adapter.

Further alternatives of the sensor adapter are illustrated in FIGS. 13 to 15. These alternatives are generally indicated with reference sign 110. The sensor adapter 110 also comprises an accommodating channel 20. The accommodating channel 20 is configured in the same manner as above described. The accommodating channel 20 is closed off in its shown end region by means of an elastic semipermeable membrane 132. The elastic semipermeable membrane 132 comprises or forms an elastically expandable cavity 134. The cavity 134 projects over the end of the accommodating channel 20 in its axial direction. The cavity 134 is dimensioned in such a way that a part of the sensor 5 can be received therein.

Figure 17:
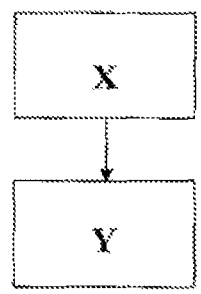
FIG. 17 shows a flow diagram of a preferred method of installing the sensor in the sensor adapter according to FIGS. 13 and 15.

To this end, the sensor 5 is pushed or inserted in the accommodating channel 20 first (step X in FIG. 17). Thereafter, the sensor 5 is further displaced or moved into the cavity 134. Since the diameter dM of the cavity 134 is smaller than the diameter dS of the sensor 5, the membrane 132 is elastically expanded in the area of the cavity 134. Similar to a rubber glove, the cavity 134 expands or dilates and optimally adapts itself to the shape of the sensor 5. Since the membrane 132 completely and circumferentially abuts the sensor 5 in the area of the cavity 134, at least the end region of the sensor 5 is tightly enclosed.

Figure 16:
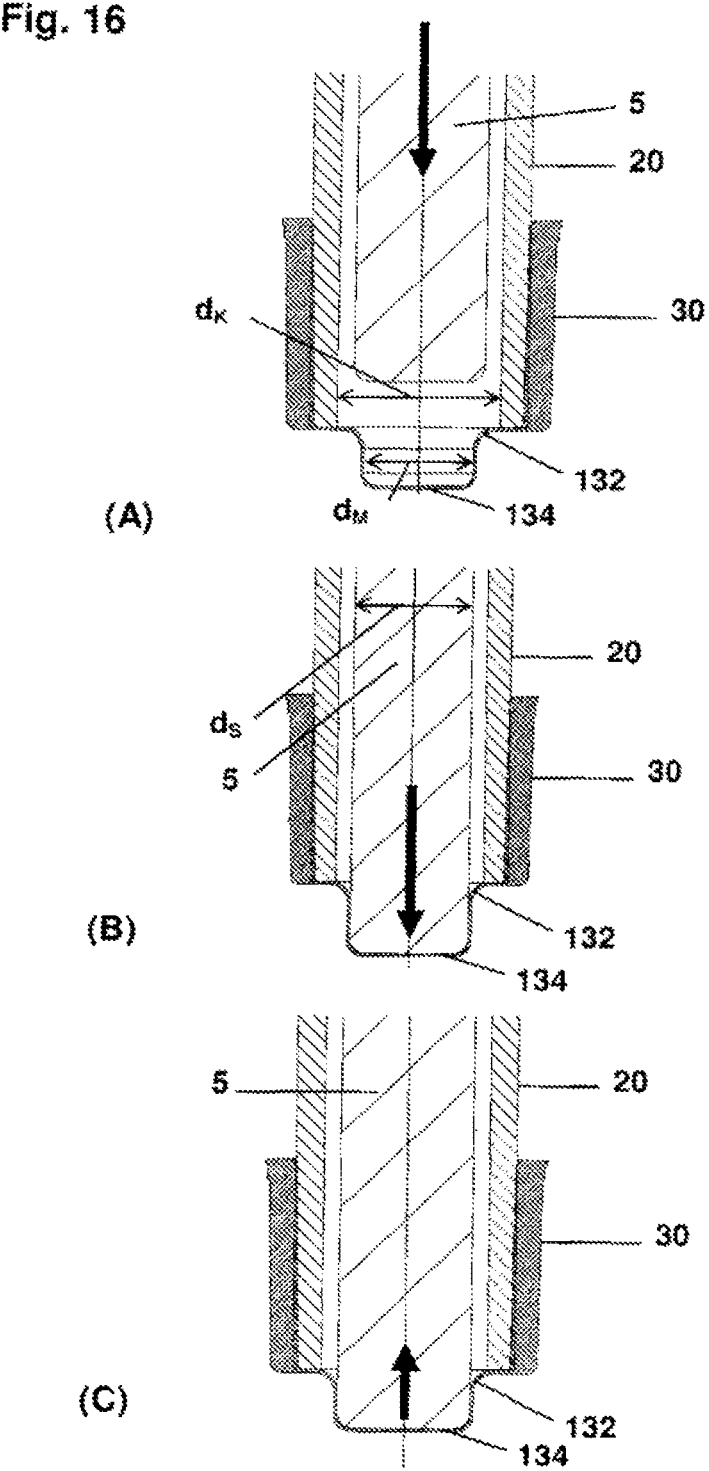
FIG. 16 shows a preferred representation of sequences of the process of inserting the sensor in the sensor adapter.

In order to guarantee this elastic and close fit of the membrane 132 with cavity 134 onto the sensor 5, the cavity 134 is correspondingly dimensioned. The inner diameter dM of the cavity 134 is preferably smaller than the inner diameter dK of the accommodating channel 20 (see FIG. 16). It is further preferred that the inner diameter dM of the cavity 134 is smaller than the outer diameter dS of the sensor 5. According to a further preferred embodiment, the inner diameter dM of the cavity 134 runs perpendicular to the longitudinal axis L of the accommodating channel 20 and ranges between 90% and 30% of the inner diameter dK of the accommodating channel 20, preferably ranges between 80% and 30%, further preferred between 70% and 30% and most preferred between 60% and 40% of the inner diameter dK of the accommodating channel 20.

Preferably, the sensor 5 is moved into the elastically expandable cavity 134 until the end face of the sensor 5 directed to the membrane 132 abuts the membrane 132. This arrangement guarantees that no air is enclosed between the membrane 134 and the sensor 5 to distort any measurements.

According to FIGS. 13 and 14, the semipermeable membrane 132 is attached to a cap 30. The cap 30 is mounted to the accommodating channel 20 to close off the sensor adapter 110 at one side. FIG. 14 shows a preferred construction of the sensor adapter 110 in an exploded view.

According to the embodiment of FIG. 15, the sensor adapter 110 comprises no cap 30. Instead of that, the semipermeable membrane 132 including the elastically expandable cavity 134 is directly attached to the accommodating channel 20. The accommodating channel 20 and the membrane 132 are preferably made of silicon and they are integrally or directly connected to each other. Despite the other way of attaching the membrane 132 to the accommodating channel, said membrane 132 provides the same function as described above.

FIGS. 16A to C illustrate the insertion of the sensor 5 in the sensor adapter 110 as shown in FIG. 17. First, the sensor 5 is pushed into the accommodating channel 20 (see FIG. 16A and step X in FIG. 17). Then, the sensor 5 is further moved or pushed into the elastically deformable cavity 134 of the membrane 132 (see the arrow in FIG. 16B and step Y in FIG. 17). Thereby, the cavity 134 is closely and sealingly fitted to the outer surface of the sensor 5 based on the elastic dilatation caused by the shape of the sensor 5. The sensor 5 is preferably moved to a position in the accommodating channel 20 where the membrane 134 completely abuts to an axial face of the sensor 5. According to FIG. 16C and after the installation of the sensor 5 in the sensor adapter 110, the sensor 5 is displaced in an axial direction by means of the elastic restoring force of the membrane 132. This is indicated by the arrow in FIG. 16C. This displacement is not as large as to remove the sensor 5 out of the elastically expandable cavity 134 of the membrane 132. Therefore, the sensor 5 is still tightly enclosed by the membrane 132, 134.

Figure 18:
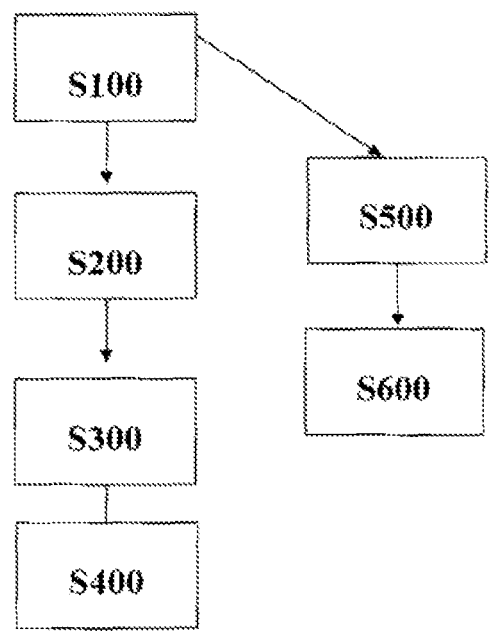
FIG. 18 shows a flow diagram of a preferred method of producing the sensor adapter according to FIGS. 13 and 15.

The manufacture of the sensor adapter 110 is schematically illustrated in the flow diagram of FIG. 18. Both embodiments of FIGS. 13 and 14 are manufactured by means of different production routes.

First, a plastic tube 20, preferably a silicon tube, is provided in step S100. Thereafter, a hollow cylindrical end cap or cap 30 is shaped in step S200. This cap 30 is closed off at one face by means of the semipermeable membrane 132 having the elastically expandable cavity 134 (step S300). In order to close off the end region of the plastic tube 20 by means of the semipermeable membrane 132, the hollow cylindrical cap or end cap 30 is mounted onto the end region of the plastic tube 20 (step S400).

According to a further production route for manufacturing the embodiment of FIG. 15, also a plastic tube 20 is provided first (step S100). Thereafter, the semipermeable membrane 132 with elastically deformable cavity 134 is made (step S500). Finally, the semipermeable membrane 132 is directly attached to the end region of the plastic tube 20 (step S600).

The invention claimed is:

1. A sensor adapter for a noninvasive positioning of a sensor in a medium, said sensor adapter comprising:
   a) an accommodating channel, in which the sensor can be positioned and axially moved therein, said accommodating channel having an end region which is closed off by a semipermeable membrane, and
   b) a hollow cylindrical sealing structure, which is disposed within said accommodating channel coaxially with the longitudinal axis thereof and with which the sensor can be disposed gas-tight adjacent to the semipermeable membrane, the semipermeable membrane being elastically deformed in the longitudinal direction of the accommodating channel when contacted by the sensor, the hollow cylindrical sealing structure having:
   a peripheral groove disposed in a radial inner wall, and
   a sealing ring disposed in the peripheral groove, said sealing ring being shiftable in the axial direction of the sealing structure between a first position and a second position, the first position and the second position being disposed adjacent to one another in the axial direction of the hollow cylindrical sealing structure, the first position being closer than the second position to the membrane, and in which the depth of the peripheral groove in the radial direction of the sealing structure is different in each of the first and second positions, with the peripheral groove being deeper than the cross section of the sealing ring in the first position so that a gap is formed between the sealing ring and the radially adjacent wall of the peripheral groove through which air can escape, and in which the peripheral groove is not as deep as the cross section of the sealing ring in the second position, such that the sealing ring is compressed in the second position between the sensor and a radial inner wall of the groove, so that the volume of the accommodating channel between the sealing ring and the semipermeable membrane is closed off gas tight.

2. The sensor adapter of claim 1, wherein the sealing structure has at least one connecting channel, at the front side facing the semipermeable membrane, the at least one connecting channel being connected with the groove.

3. The sensor adapter of claim 1, wherein the sealing structure forms a supporting sleeve, which is disposed in the end region of the accommodating channel and with which the accommodating channel can be supported laterally.

4. The sensor adapter of claim 1, wherein the semipermeable membrane is disposed at a front side of the sealing structure, so that the accommodating channel can be closed off by the sealing structure.

5. The sensor adapter of claim 1, wherein the accommodating channel consists of a plastic tube, which is closed off at one side by a hollow cylindrical cap with the semipermeable membrane, so that the sealing structure and the hollow cylindrical cap support one another in the radial direction over the plastic tube.

6. A bioreactor in combination with the sensor adapter of claim 1.

7. A method for inserting a sensor in the sensor adapter of claim 1, said method comprising the following steps:
   a) pushing the sensor into the accommodating channel,
   b) shifting the sealing ring into the first position by pushing the sensor into the accommodating channel,
   c) displacing a medium from the accommodating channel, in that the sensor is moved in a direction towards the semipermeable membrane, and
   d) moving the sensor in a direction away from the semipermeable membrane, so that the sealing ring is shifted into the second position and seals the sensor in the accommodating channel.

8. The method of claim 7, wherein the sensor is moved at least until it touches the semipermeable membrane, deforming the semipermeable membrane elastically, in order to displace the medium between the sensor and the semipermeable membrane from the accommodating channel during said displacing step.

9. A The sensor adapter according to claim 1, wherein the semipermeable membrane comprises an elastically expandable cavity in which a part of the sensor can be received, such that the semipermeable membrane tightly encloses a received part of the sensor.

10. The sensor adapter according to claim 9, wherein the elastically expandable cavity of the membrane has a diameter perpendicular to the longitudinal axis of the accommodating channel which is smaller than the inner diameter of the accommodating channel, and smaller than an outer diameter of the received part of the sensor.

11. The sensor adapter according to claim 10, in which the diameter of the cavity perpendicular to the longitudinal axis of the accommodating channel ranges between about 90% and 30% of the inner diameter of the accommodating channel.

12. The sensor adapter according to claim 9, wherein the semipermeable membrane is integrally connected to one of the accommodating channel or a hollow cylindrical cap.

13. A method for inserting a sensor in a sensor adapter of claim 9, said method comprising the following steps:
   a) pushing the sensor into the accommodating channel,
   b) pushing the sensor in the expandable cavity of the membrane so that the sensor is at least partly and tightly enclosed by the membrane.

14. The method according to claim 13, in which the pushing the sensor in the expandable cavity step includes the further step of: moving the sensor into the expandable cavity of the membrane so that the membrane abuts a face of the sensor.

15. The sensor adapter of claim 1, in which the sensor is an electrochemical sensor.

16. The sensor adapter of claim 5, wherein the plastic tube is a silicone tube.

* * * * *